(12) United States Patent
Serlachius

(10) Patent No.: US 8,590,980 B2
(45) Date of Patent: Nov. 26, 2013

(54) CHAIR BACK SUPPORT SYSTEM

(76) Inventor: Jarl Fredrik Serlachius, Kauniainen (FI)

( * ) Notice: Subject to any disclaimer, the term of this patent is extended or adjusted under 35 U.S.C. 154(b) by 243 days.

(21) Appl. No.: 13/147,610

(22) PCT Filed: Feb. 4, 2010

(86) PCT No.: PCT/FI2010/000008
§ 371 (c)(1),
(2), (4) Date: Aug. 3, 2011

(87) PCT Pub. No.: WO2010/089447
PCT Pub. Date: Aug. 12, 2010

(65) Prior Publication Data
US 2011/0291449 A1    Dec. 1, 2011

(30) Foreign Application Priority Data

Feb. 4, 2009   (FI) ...................................... 20090034

(51) Int. Cl.
*A47C 7/44*   (2006.01)
(52) U.S. Cl.
USPC .......................... 297/464; 297/411.1; 602/36
(58) Field of Classification Search
USPC ...................... 297/411.1, 464; 602/19, 32, 36
See application file for complete search history.

(56) References Cited

U.S. PATENT DOCUMENTS

| | | | | |
|---|---|---|---|---|
| 806,713 | A | * | 12/1905 | Pohle ............................. 297/464 |
| 1,722,205 | A | * | 7/1929 | Freund ............................. 602/19 |
| 2,667,913 | A | | 2/1954 | Dustin |
| 2,667,917 | A | * | 2/1954 | Dustin ....................... 297/411.1 |
| 3,063,752 | A | | 11/1962 | Moore |
| 3,767,260 | A | * | 10/1973 | Limpach ..................... 297/411.3 |
| 4,583,533 | A | * | 4/1986 | Goodley et al. ................. 602/36 |
| 4,996,978 | A | * | 3/1991 | Gingras .......................... 602/19 |
| 5,380,269 | A | * | 1/1995 | Urso ......................... 297/411.31 |
| 5,746,480 | A | * | 5/1998 | Bonutti .................... 297/411.35 |
| 5,975,639 | A | * | 11/1999 | Wilson et al. ............ 297/411.35 |
| 6,315,750 | B1 | | 11/2001 | Gray |
| 6,332,232 | B1 | * | 12/2001 | Neal ........................ 297/411.23 |
| 7,416,257 | B1 | * | 8/2008 | Lakhman ...................... 297/487 |

FOREIGN PATENT DOCUMENTS

| | | |
|---|---|---|
| CA | 510854 | 3/1955 |
| DE | 2410839 | 9/1975 |
| WO | WO 2005115560 | 12/2005 |
| WO | WO 2008042663 | 4/2008 |
| WO | WO 2010089447 | 8/2010 |

\* cited by examiner

*Primary Examiner* — Peter Brown
(74) *Attorney, Agent, or Firm* — Seppo Laine Oy; Joshua P. Wert

(57) ABSTRACT

The invention consists of a chair back support, which consists of at least two flexible elongated supports (2,2*a*) on both sides of the seat (1), which supports (2, 2*a*) are connected with support belts (3, 3*a* and 4, 4*a*), all supporting a person's back and making gymnastic movements possible both for the back and stomach while sitting on the chair.

8 Claims, 2 Drawing Sheets

CHAIR BACK SUPPORT SYSTEM

FIELD OF INVENTION

A chair back support, which, in addition to supporting the back, also strengthens both the abdomen and the back muscles.

BACKGROUND OF THE INVENTION

When, in the course of development, man started to stand up and walk on two legs there is one part of the body, which, even up to today, has not fully adjusted to this change. As, in ancient times, man divided his body weight between his four legs, the support system of his body could well cope with the load on it. It is different for man today: he regularly has to bend down from a height, often with a heavy load on him. Everybody can understand that the lumbar region, which always has to act as a hinge, cannot well cope with it. An enormous torsion load on the lumbar and pelvic vertebrae lends them to easy injury. However, man has to learn to live with his lumbar region and to support its functions as best as he can. The most efficient way to keep one's back in good condition is to prevent any injuries and degenerations by strengthening the muscles supporting the spine. This way, it is possible to transfer any load from the vertebrae to the muscles supporting them.

Another way to take care of one's back is to work in a position which is as friendly to the back as possible. Also in this respect, as the entire concept of working which sitting was non-existent, the ancient man was in a better position than modern man. Today, most work is performed in a sitting position. When working while sitting, the back often has to be in a bent position impacting load on the lower back.

True, modern ergonomic chairs support the back well, but not enough. Therefore, a chair is continuously being developed, with the latest result being the saddle chair. In its design, the idea of support for the back has been disregarded; instead, the idea is to lend the back as good a posture which does not at all require a support element on the back of the chair. The chair works for some people, but it has not gained extensive popularity. The reason for this is that it is impossible to work at a desk for a whole day with a straight back.

The purpose of the invention presented here is to show a solution to sitting in a bent position.

SUMMARY OF THE INVENTION

This is achieved with a chair back characterized in that the chair back support consists of a minimum of two at least partially flexible, elongated supports on both sides of the seat and the upper halves of the supports are covered with padding, are freely movable, and not connected to each other, and the bottom ends of the supports are anchored to be adjustable both to the front and to the back along the seat and in proportion to their angle to the seat, and the lower halves of the supports are connected with at least one support belt, adjustable both longitudinally and up and down along the supports.

It is beneficial for the elongated supports to be somewhat flexible; hence, glass fibre type materials or thin steel or wood is well suited for them. The profile suited for steel and wood is flat and thin and for pipes for glass fibre and carbon fibre. It is good to cover the areas touching man's body with some nice, soft material. The longitudinal supports must be mounted so that the supports are located on the sides of the seat, preferably in the mid-point area or backwards from it, however, in the manner that, as necessary, it is possible to place them either in front or in the back of the shoulders. For the system to function, it is not important where the longitudinal supports are anchored. They can be anchored under the seat, on the chair leg, or on the side of the seat. It is possible for the longitudinal supports to be part of a removable seat, which can be fitted on top of the seat in a regular chair. In order not to have to stand up from the chair or remove or open the belt, when the support belt is moved from the stomach side to the back side or vice versa, it is beneficial to have two support belts on top of each other. Technically, the best solution for it is that a belt is fastened in the middle of both longitudinal supports, which leaves two belt flaps which can be fastened with Velcro tape on the corresponding side flap on the other support. This creates two independently operating support belts, one for the back and the other one for the abdomen, which, as necessary, can be easily opened and fastened.

As was already stated, flexibility in the elongated supports is achieved by using flexible material and by only fastening the other ends of the elongated supports. Another possibility is to have the elongated supports made of stiff material and to do the actual fastening with a spring or with a flexible supplementary part. In order for the lumbar region to always have support, it would be beneficial to be able to adjust the support belt horizontally. This can be achieved with the help of the elongated supports, if they are fastened with a joint to the chair or seat, which enables forward and backward adjustment of the elongated supports.

In order to allow the locking of the elongated supports into the desired angle and place, the recommendable method to mount the elongated supports onto the chair is to use a metal bushing with an axle or joint or a similar arrangement with tension screws. For practical reasons, it is possible to connect the elongated supports, e.g., with a bushing-fastened brace or axle running under the chair's seat. This way, both elongated supports are simultaneously adjusted. If the goal is to make the chair multifunctional, it is possible to fasten and bushings onto a rail-like element, allowing the moving of the elongated pipes forwards and backward on the rail and the locking thereof on the favorite place.

With this type of system, man can support his back in two ways. He can either position himself in front of the elongated supports, in which case the support belt in front of him supports his body against falling forward. He can either place himself in front of the elongated support, in which case the support belt on the abdomen side in the front prevents the body from falling forwards. Or, he can position himself behind the elongated supports, in which case the elongated supports prevent him from leaning forwards. As a result of the powers, the support belts located on opposite sides act as a counter power for the person to stay in place.

The system allows the stimulation of a tired back through exercise, allowing regenerating flow of blood. Hence, it is possible to refresh the body by exercising during breaks. With the elongated supports on the back side and the support belt on the abdomen side, it is possible to bend the body from the waist backwards, with the elongated supports generating a resistance. This way, the deep back muscles are activated. And vice versa, with the elongated supports in the front and the support belt on the back side, it is possible to bend the back forward from the lumbar, activating the deep abdominal muscles.

This way, a tired back receives new blood and does not get tired during work.

The following is a presentation of the invention, with reference to the attached drawings, in which

DETAILED DESCRIPTION OF EXEMPLARY EMBODIMENTS

Figure 1:
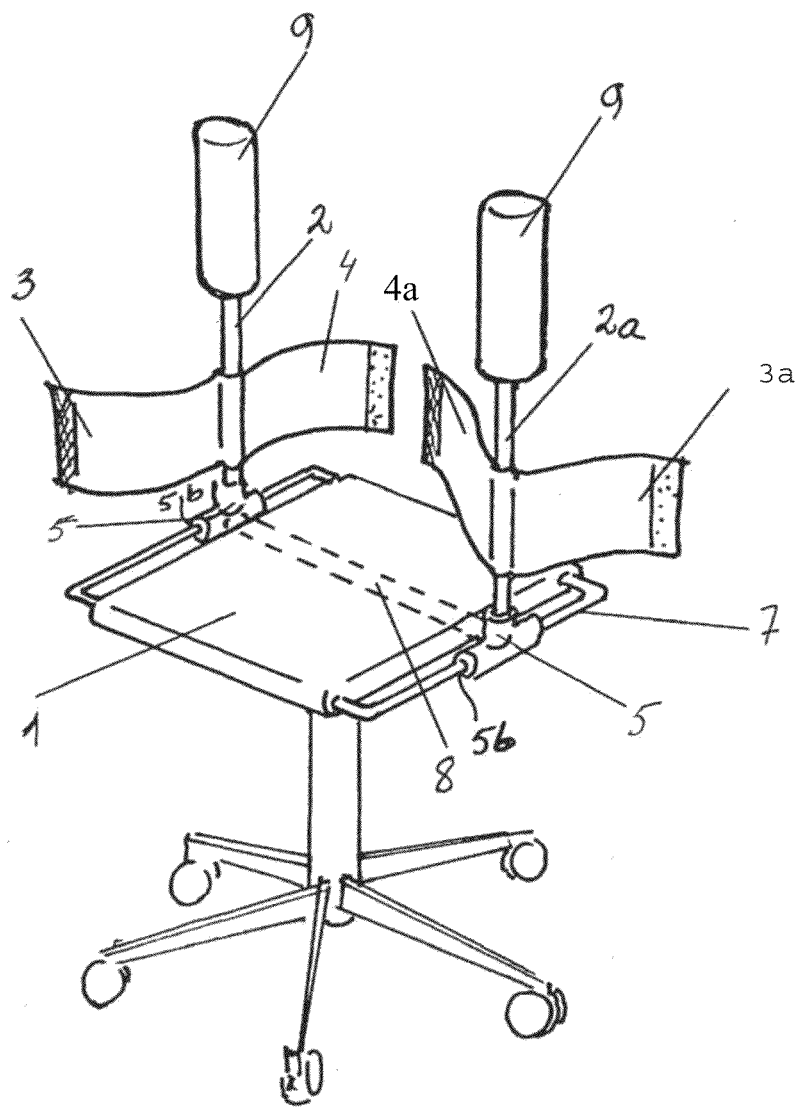
FIG. 1 presents a regular chair, consisting of two elongated supports, with support belts.

FIG. 1 presents a chair (1), onto which flexible elongated supports (2, 2a), with padding (9), are fastened with bushings (5, 5a) or suchlike. There is a pair of support belts (3, 3a and 4, 4a), adjustably mounted at the same level onto the frame of the elongated supports (2, 2a), longitudinally adjustable with Velcro tape. There is a railtype element (7) on the side of the chair's seat (1), along which (5b) the bushings (5) mounted on it can be moved.

There is an axle (8) under the seat (1), which connects the bushing 6).

Figure 2:
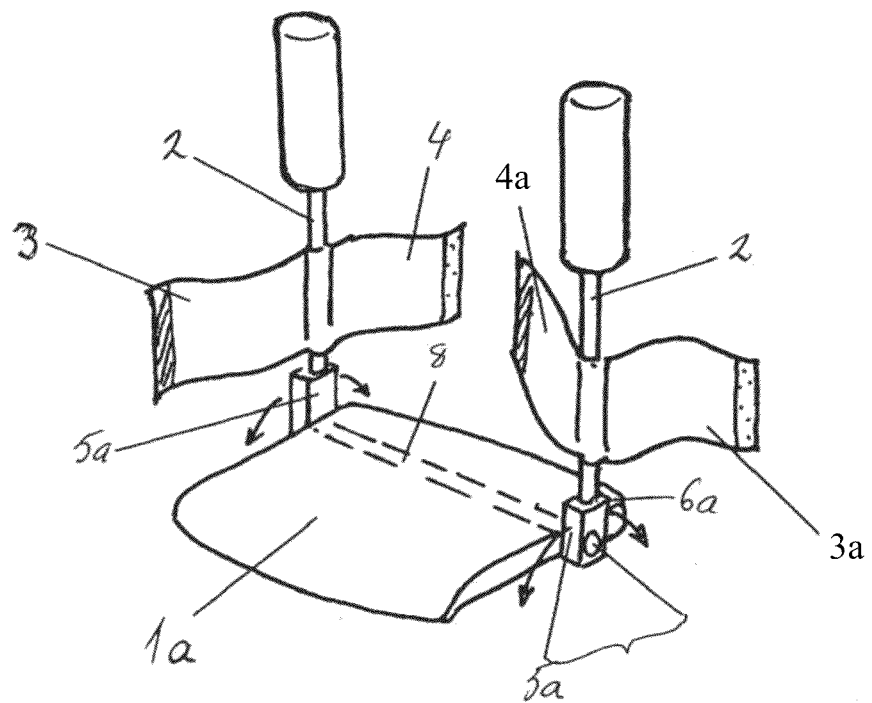
FIG. 2 presents a removable seat, with flexible elongated supports and support belts.

FIG. 2 shows a removable seat solution (1a). It has the same elements as in FIG. 1 and, additionally, a bushing with a joint (5a), attached directly to the back corner (6a) of the seat (1a).

The intention of the clarification, with the related drawings, is to illustrate the idea according to the invention. The details in the support system according to the invention may vary within the framework of the claims.

The invention claimed is:

1. A chair back support system consisting of;
   at least two at least partially flexible, elongated supports on both sides of a seat, said supports having upper halves which are covered with padding, and wherein the at least two supports are freely movable,
   wherein said supports have bottom ends which are anchored and adjustable both in a forwards and a backwards direction along the seat, and
   wherein said supports have lower halves which are connected with at least one first support belt which is adjustable at least in an upwards and downwards direction along the supports.

2. A chair back support system according to claim 1, wherein the elongated supports are each mounted, by a bushing with a joint or an axle, onto a frame or the seat and wherein said bushing is further mounted onto a rail-type element surrounding the seat along which the bushing can be moved, wherein said bushings can be further connected, with an axle, to each other allowing simultaneous adjustment of both supports.

3. A char back support system according to claim 2, wherein the lower parts of the supports are connected with a second support belt at the same adjustable level as the first support belt.

4. A chair back support system according to claim 1, wherein the lower parts of the supports are connected with a second support belt at the same adjustable level as the first support belt.

5. A chair back support system according to claim 4, wherein the pair of support belts are a hook-and-loop fastening tape.

6. A chair back support system according to claim 4, wherein the elongated supports are mounted on a separate seat bench which can be fitted on top of a separate chair.

7. A chair back support system according to claim 1, wherein the supports are entirely made of a highly flexible material.

8. A chair back support system according to claim 1, wherein the elongated supports are mounted on a separate seat bench which can be fitted on top of a separate chair.

* * * * *